US00PP09129P

United States Patent [19]

Friday

[11] Patent Number: Plant 9,129

[45] Date of Patent: May 9, 1995

[54] 'P. F. 1'PEACH TREE

[76] Inventor: Paul J. Friday, P.O. Box 850, Coloma, Mich. 49038

[21] Appl. No.: 266,721

[22] Filed: Jun. 24, 1994

[51] Int. Cl.[6] ..... A01H 5/00
[52] U.S. Cl. ..... Plt./43.1
[58] Field of Search ..... Plt. 43.1

*Primary Examiner*—James R. Feyrer
*Attorney, Agent, or Firm*—Fred P. Kostka

[57] ABSTRACT

A new and distinct variety of peach tree having the following unique combination of desirable features:

1. Producing a very firm fruit having a resilient flesh texture.
2. Blossoms are non-showy when in full bloom.
3. A substantially oval spheroidal fruit with an attractive red skin coloring over a majority of the surface.
4. Early maturing fruit of good taste.
5. An early maturing (before maturity of Redhaven peach) fruit of good storage and shelf life.

1 Drawing Sheet

ORIGIN OF VARIETY

The new variety of peach tree (hereinafter referred to as the P. F. 1 peach tree) was originated by Paul Friday in the experimental orchard maintained for the purpose of breeding peaches at Paul Friday Farms Inc. located in Coloma, Mich. Coloma is located in the southwest section of Michigan. The P.F. 1 peach tree was developed in a first generation cross between the female parent, Garnet Beauty, and the male parent, Cardinal.

ASEXUAL REPRODUCTION OF THE VARIETY

The new and distinct variety of peach tree was asexually propagated by budding as performed in the experimental orchard of Paul Friday Farms Inc. located in Coloma, Mich. The asexual propagation demonstrates that such reproduction of the characteristics of the tree are consistent and are established and transmitted through succeeding propagation.

SUMMARY OF THE VARIETY

The new and distinct variety of peach tree is of moderate upright growth and a regular and productive bearer of peaches. The blossoms are characterized by being contracted or partially spread when in full bloom. At the same time the petals of the blossoms are of lesser length than the length of petals of the normal showy blossom as exemplified by the Loring peach blossom.

The blossoms of the present peach tree at full bloom may be characterized as being non-showy. More specifically, the blossoms of the present peach tree have radially projecting and angularly spaced five blossom petals projecting upwardly at an inclined angle so as to form a blossom having a diameter of about ½" measured across the blossoms. The bloom is even less showy than the non-showy Redhaven.

The flesh of the fruit of the present peach tree is firm and is yellow.

The skin is smooth and is of dark red color over about ninety (90%) percent of its surface at maturity. The dark red color occurs over about seventy (70%) percent of the surface about 10 days prior to maturity. At maturity the peach is spheroid with an oval shape having an elongated diameter ranging between about 2¼" and 2⅝".

The fruit has a firm flesh and may be described as resilient to the extent that the flesh is yieldable and restorable to its original state when subjected to impact forces which may cause permanent deformities in peaches of the commercial varieties. The firmness of the fruit facilitates handling and packaging of the peaches without damaging the same for shipment. This results is less spoilage and also increases the shelf life.

The fruit matures in the early part of the peach growing season of Sourthwestern Michigan. The fruit as mentioned heretofore is of red color over about ninety (90%) percent of its surface and has a very attractive appearance.

The fruit shows a particularly strong resistance to the disease, bacterial spot, and has fewer split pits than other early varieties of peaches grown in Michigan (approximately only two (2%) percent of the fruit show split pits).

BRIEF DESCRIPTION OF THE PHOTOGRAPHS

The accompanying drawing comprises a top photographic illustration which shows fruit, foliage and twigs of the new variety, with the upper and lower surfaces of the leaves being illustrated, five whole peaches in mature stage attached to the stems in varying orientations to show the shape of the fruit, and portions of fruit cut along the plane of the suture to show the internal stone attachment and flesh characteristics. The bottom photograph shows a specimen of fruit split on the plane of the surface, at about a stage of ripeness for harvesting, and shows in larger scale, the flesh color, stone and stone cavity along with an adjacent ruler to give an indication of size of both the whole fruit and stone. The illustrations were taken shortly after being picked at a firm ripe maturity stage and with the colors being as nearly true as reasonably possible in photopraphic color representations of this type.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panatone Matching System (PMS) as used internationally to identify printed colors.

Tree:

*Height.*—Unpruned 15'.

*Width.*—Unpruned 12'.
*Size.*—Medium-large.
*Vigor.*—Medium vigor terminal growth of 1' to 4' per year.
*Density.*—Medium, pruning requirements heavy.
*Form.*—Upright.
*Production.*—Productive, approximately ½ of the fruit annually must be thinned off to obtain the size decribed.
*Bearer.*—consistent.
*Disease resistance to bacterial leaf and fruit spot.*—Very good.

Trunk:
*Size.*—Medium to stocky.
*Surface.*—Smooth to medium shaggy.

Branches:
*Size.*—Medium.
*Surface.*—Smooth to medium.
*Lenticels.*—Medium number and medium size.
*Color.*—Grayish brown.

Leaves:
*Size.*—Large. Average length — 6" to 7". Average width — 1½".
*Form.*—Lanceolate — pointed.
*Thickness.*—Medium.
*Texture.*—Medium.
*Margin.*—Serrate.
*Petiole.*—Medium length-medium thickness.
*Gland.*—Predominantly 2, one on each side of the base of the leaf.
*Color.*—Upper surface: green (350c). Surface: dull green (349c).

Flower buds:
*Size.*—Medium.
*Length.*—Medium.

Flowers:
*Blooming period.*—Apr. 7, 1993 to Apr. 14, 1993.
*Size.*—Non-showy petal pattern (about ½" diameter).
*Pollen.*—Present, self-fertilizing.
*Color.*—Pink.

Fruit:
*Maturity when described.*—Firm ripe.
*Date of first picking.*—Jul. 15, 1993 (About 21 days before picking Redhaven — Aug. 8, 1993.
*Date of last picking.*—Jul. 22, 1993.
*Size.*—Medium sphere. Average diameter — 2-⅜".
*Form.*—Spherical oval.
*Suture.*—Medium.

Skin:

*Thickness.*—Medium.
*Texture.*—Medium.
*Tendency to crack.*—None.
*Down.*—Moderate to little.
*Color.*—Yellow ground color (134c). Nearly overspread (80%) with red (174c) to (173c).

Flesh:
*Texture.*—Firm.
*Ripens.*—Relatively even.
*Flavor.*—Good.
Aroma.—Pleasant.
*Eating quality.*—Excellent.
*Color.*—Yellow (14c) to (13c). Pit cavity pink yellow (15c).

Stone:
*Type.*—Semi-cling.
*Size.*—Average length 1½". Average width — 1". Average thickness — ½".
*Form.*—Ovid.
*Base.*—Straight.
*Apex.*—Pointed.
*Sides.*—Nearly equal.
*Surface.*—Irregularly furrowed.
*Color.*—Brown to reddish brown.
*Tendency to crack.*—None to negligible.

Use: Desert.
Shipping quality: Good.
Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described as medium-large size, medium upright in growth and a regular and productive bearer of medium large size, yellow flesh semi-cling fruit, good flavor and eating quality; and being further characterized by a non-showy blossom about ½ inch in diameter when in full bloom, said fruit as maturity is of substantially oval spheroidal shape with firm flesh and red skin color covering 90% of the fruit, said maturity occuring about 21 days before maturity of the Redhaven.

* * * * *

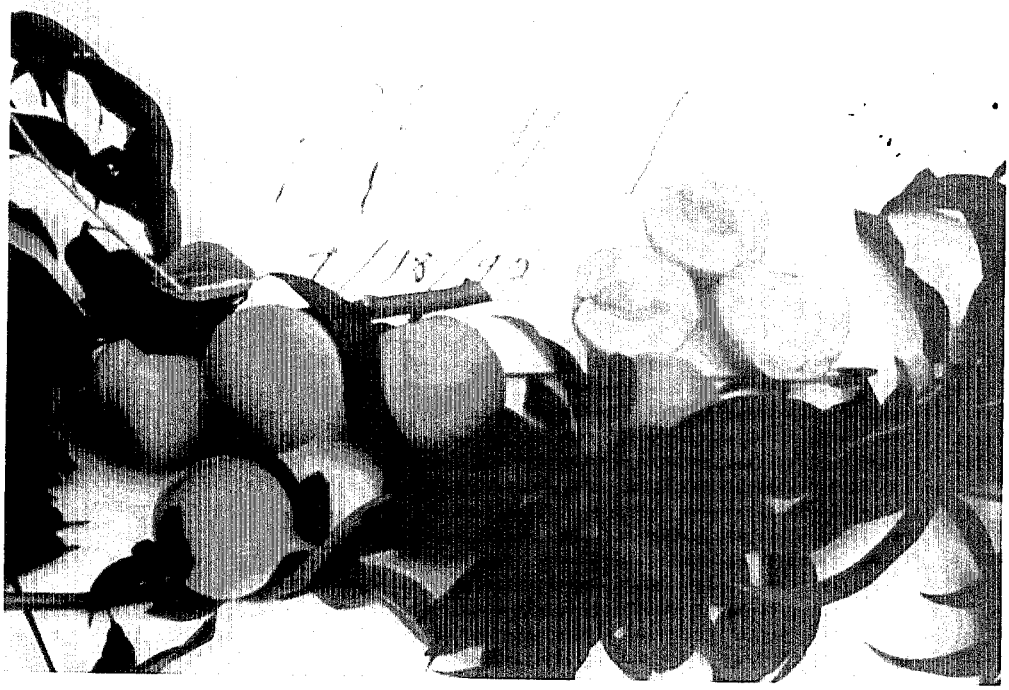
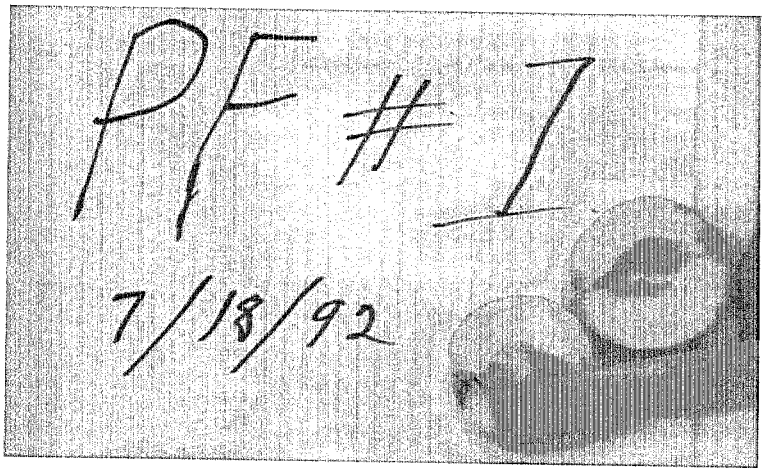
PF #1
7/18/92